(12) United States Patent
Taketani et al.

(10) Patent No.: US 6,333,437 B1
(45) Date of Patent: Dec. 25, 2001

(54) METHOD FOR PURIFYING A BROMINE COMPOUND

(75) Inventors: Yutaka Taketani; Haruhisa Hoshimi; Akihiro Mukai; Yasuhisa Tahira; Takahiro Sato, all of Tokyo (JP)

(73) Assignee: Teijin Chemicals LTD, Tokyo (JP)

( * ) Notice: Subject to any disclaimer, the term of this patent is extended or adjusted under 35 U.S.C. 154(b) by 0 days.

(21) Appl. No.: 09/657,511

(22) Filed: Sep. 7, 2000

Related U.S. Application Data

(63) Continuation of application No. 09/177,573, filed on Oct. 23, 1998, now abandoned.

(30) Foreign Application Priority Data

| Oct. 28, 1997 | (JP) | .................................................... 9-295402 |
| Oct. 28, 1997 | (JP) | .................................................... 9-295403 |
| Sep. 1, 1998  | (JP) | ................................................... 10-003181 |

(51) Int. Cl.$^7$ .................................................... C07C 41/34
(52) U.S. Cl. ......................... 568/634; 568/633; 568/643; 568/645; 568/646
(58) Field of Search ................................ 568/633, 634, 568/643, 645, 646

(56) References Cited

FOREIGN PATENT DOCUMENTS

| 0572154A  | 12/1993 | (EP) . |
| 49125348  | 11/1974 | (JP) . |
| 55111429  | 8/1980  | (JP) . |
| 57289     | 1/1982  | (JP) . |
| 2286645   | 11/1990 | (JP) . |
| 4234337   | 8/1992  | (JP) . |
| 7291884   | 11/1995 | (JP) . |
| 7316087   | 12/1995 | (JP) . |
| 8113547   | 5/1996  | (JP) . |

OTHER PUBLICATIONS

Database WPI, Week 9606, Derwent Publications, Ltd., London, GB; & JP 07 316087A (Tosoh Corp.), Apr. 1, 1994 (Abstract).

Database WPI, Week 9240, Derwent Publications, Ltd., London, GB; & JP 04 234337A (Tosoh Corp.), Dec. 28, 1990 (Abstract).

*Primary Examiner*—Rosalynd Keys

(57) ABSTRACT

A method for purifying a bromine compound by depositing the bromine compound represented by the following general formula (1) as solid particles from a crude solution containing the bromine compound:

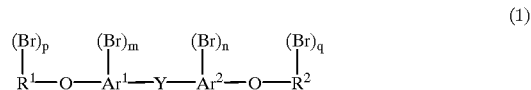

(1)

wherein (i) the crude solution is supplied into the slurry containing the particles of the bromine compound;

(ii) the concentration of the particles of the bromine compound in the slurry is maintained at a predetermined range;

(iii) the solvent contained in the slurry is a mixed solvent of a good solvent and a poor solvent and the ratio of the good solvent to the poor solvent is maintained at a predetermined value; and (iv) the solid particles of the bromine compound are separated from the slurry.

26 Claims, 1 Drawing Sheet

METHOD FOR PURIFYING A BROMINE COMPOUND

This application is a Continuation application Ser. No. 09/177,573 filed Oct. 23, 1998 now abandoned.

FIELD OF THE INVENTION

The present invention relates to a method for purifying a specific bromine compound. More specifically, it relates to a method for purifying a specific bromine compound, which is capable of obtaining a bromine compound having high purity and excellent heat stability.

PRIOR ART

Generally speaking, a bromine compound typified by an ether derivative of tetrabromobisphenol A is widely used due to its excellent performance as a flame retardant for polyolefin-based resins and styrene-based resins.

Since the heat stability of the by-product is adversely affected when the bromine compound contains a certain type of a by-product produced during its production process, various means for purifying the bromine compound have been proposed heretofore.

For instance, JP-A 49-125348 (the term "JP-A" as used herein means an "unexamined published Japanese patent application") discloses a method comprising dissolving 2,2-bis[{3,5-dibromo-4-(2,3-dibromopropyloxy)}phenyl]propane (may be abbreviated as TBA-BE hereinafter) in a ketone-based solvent and cooling the mixture to deposit a bromine compound.

JP-A 55-111429 discloses a method of adding an aromatic hydrocarbon halide solution of TBA-BE to a mixture of methanol and seed crystals.

JP-A 4-234337 discloses a method comprising adding a poor solvent having a higher boiling point than a good solvent dropwise to a solution of TBA-BE dissolved in a good solvent and recovering the TBA-BE as fine powders while the good solvent is distilled out after the completion of the addition, and JP-A 7-316087 discloses a method comprising adding a solution of TBA-BE dissolved in a good solvent dropwise to a heated poor solvent having a higher boiling point than the good solvent while the solution was stirred and dispersing TBA-BE crystals into the poor solvent to recover them while the good solvent is distilled out.

JP-A 8-113547 discloses a method of adding a solution of TBA-BE dissolved in a good solvent to heated methanol in the presence of seed crystals while the good solvent was distilled out and crystallized to recover solids having large particle diameters.

JP-A 7-291884 discloses a method comprising adding water to an organic solvent solution of TBA-BE in the presence of a surfactant to form an emulsion and removing the organic solvent to recover TBA-BE powders.

JP-A 2-286645 discloses a method of adding unpurified TBA-BE to molten TBA-BE.

Further, JP-B 57-289 (the term "JP-B" as used herein means an "examined Japanese patent publication") discloses a method comprising adding a poor solvent to a good solvent solution of TBA-BE and stirring the resulting solution with shearing force.

However, these methods require complicated operation or a large-scale apparatus, or the purity and heat stability of the obtained solid are not always satisfactory. Therefore, there has been desired a method for obtaining a bromine compound having higher purity and excellent heat stability with a simple apparatus.

SUMMARY OF THE INVENTION

The inventors of the present invention have conducted intensive studies to provide a purification method for obtaining a bromine compound having higher purity and excellent heat stability and have found that, in a method for purifying a bromine compound from a crude solution of a bromine compound, a bromine compound having high purity and excellent heat stability can be obtained by crystallizing the bromine compound while crystals contained in a slurry comprising a good solvent, a poor solvent and the crystals of the bromine compound are contained in a specific proportion and the solubility of the bromine compound in the solvents contained in the slurry falls within a certain predetermined range. The present invention has been accomplished by this finding.

That is, according to the present invention, there is provided a method for purifying a bromine compound by depositing the bromine compound represented by the following general formula (1) as solid particles from a crude solution containing the bromine compound:

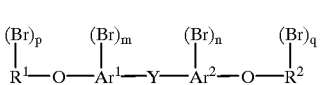

(1)

wherein $Ar^1$ and $Ar^2$ are the same or different and each an aromatic hydrocarbon group having 6 to 10 carbon atoms; Y is an alkylene group having 1 to 3 carbon atoms, single bond, sulfone group or ketone group; $R^1$ and $R^2$ are the same or different and each a hydrocarbon group having 2 to 5 carbon atoms; m and n are the same or different and each an integer of 1 to 4; and p and q are the same or different and each an integer of 2 or 4, wherein (i) the crude solution is supplied into the slurry containing the particles of the bromine compound to deposit the bromine compound in the slurry under agitation;

(ii) the concentration of the particles of the bromine compound in the slurry is maintained at 10 to 50 wt %;

(iii) the solvent contained in the slurry is a mixed solvent of a good solvent and a poor solvent for a bromine compound and the solubility of the bromine compound in the mixed solvent is maintained at 0.1 to 5 g/100 g of solvent; and (iv) the slurry is extracted to separate the solid particles of the bromine compound from the slurry.

According to the purification method of the present invention, when the obtained bromine compound is mixed with a flame retardant for resins, there will be obtained a high-purity bromine compound that neither reduces the heat stability of a resin nor causes the coloration of the resin. According to the purification method of the present invention, particularly when the bromine compound is mixed with a resin, impurities causing an adverse effect are separated into a mixed solvent, thereby making it possible to obtain a bromine compound of interest as a high-purity solid at a high yield. Further, the purification method of the present invention facilitates a continuous operation and can be carried out with a simple apparatus under mild conditions. Therefore, it is industrially advantageous.

Figure 1:
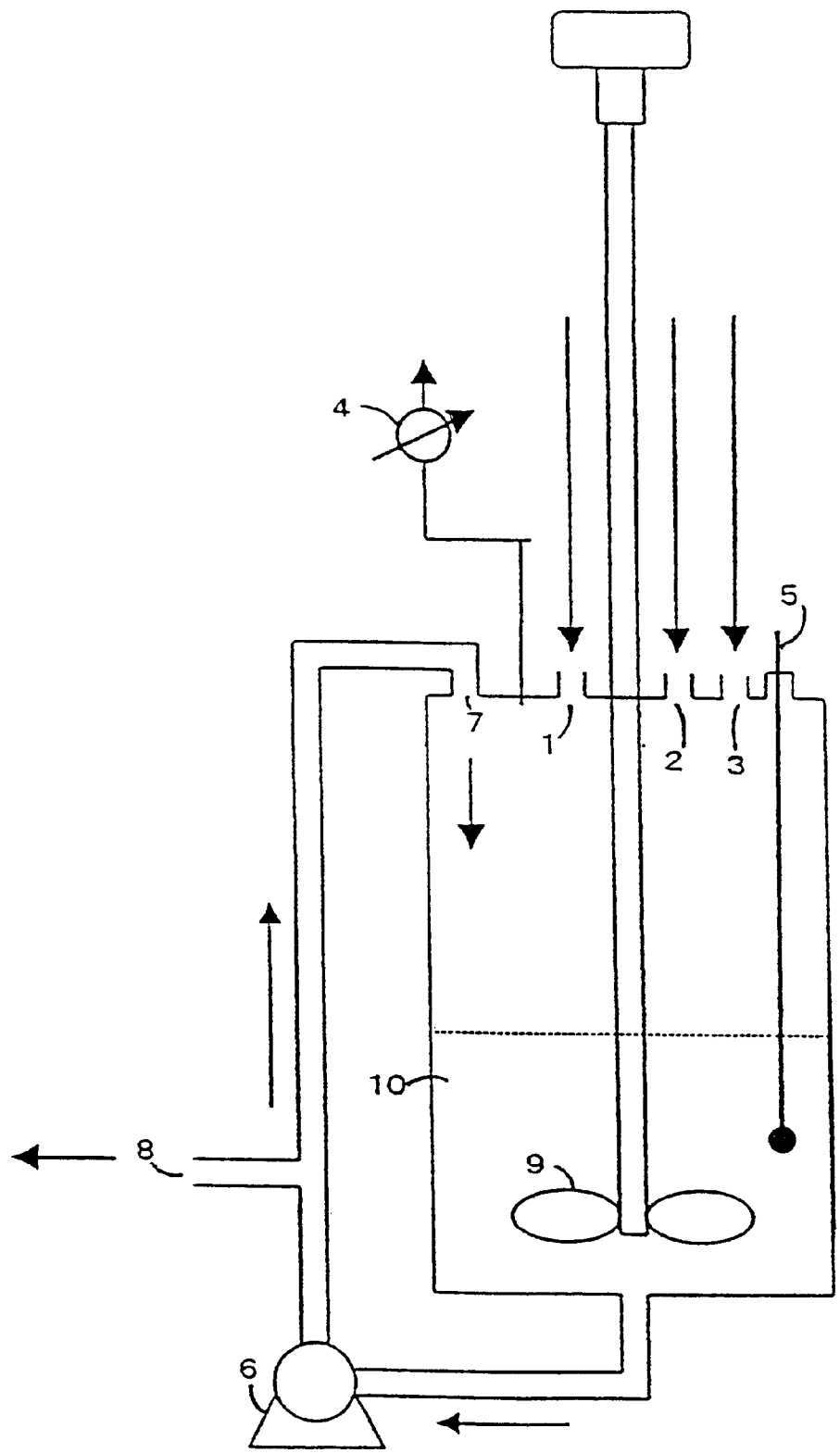
FIG. 1 shows an example of an apparatus for purifying a bromine compound in the present invention.

Numbers 1, 2 and 3 denote an input port, number 4 a capacitor, number 5 a thermometer, number 6 a pump, number 7 an input port for a recycled slurry, number 8 an output port for a slurry, number 9 a stirrer and number 10 a slurry.

The present invention will be described in detail hereinafter.

The bromine compound to be purified in the present invention is represented by the above general formula (1). In the above general formula (1), $Ar^1$ and $Ar^2$ are the same or different, and each an aromatic hydrocarbon group having 6 to 10 carbon atoms, as exemplified by benzene, monomethyl-substituted benzene, dimethyl-substituted benzene and naphthalene. Of these, benzene is preferred. Y is a bond or group for combining $Ar^1$ and $Ar^2$, as exemplified by an alkylene group having 1 to 3 carbon atoms, single bond, sulfone group and ketone group. Of these, methylene group and isopropylidene group are preferred. $R^1$ and $R^2$ are the same or different and each a hydrocarbon group having 2 to 5 carbon atoms, as exemplified by ethyl group, propyl group, isopropyl group, butyl group and isobutyl group. Of these, an ethyl group and propyl group having 2 or 3 carbon atoms are preferred. m and n are the same or different, and each an integer of 1 to 4, preferably 1 or 2. p and q are the same or different, and each an integer of 2 or 4, preferably 2.

Illustrative examples of the bromine compound include 2,2-bis[{3,5-dibromo-4-(2,3-dibromopropyloxy)}phenyl]propane, 2,2-bis[{3,5-dibromo-4-(2,3-dibromo-2-methylpropyloxy)}phenyl]propane, bis[{3,5-dibromo-4-(2,3-dibromopropyloxy)}phenyl]methane, bis[{3,5-dibromo-4-(2,3-dibromo-2-methylpropyloxy)}phenyl]methane, bis[{3,5-dibromo-4-(2,3-dibromopropyloxy)}phenyl]sulfone, bis[{3,5-dibromo-4-(2,3-dibromo-2-methylpropyloxy)}phenyl]sulfone, {3,3',5,5'-tetrabromo-4,4'-(2,3-dibromopropyloxy)}biphenyl, {3,3',5,5-tetrabromo-4,4'-(2,3-dibromo-2-methylpropyloxy)}biphenyl, {3,3',5,5'-tetrabromo-4,4'-(1,2-dibromoethyloxy)}biphenyl and the like. Of these, 2,2-bis[{3,5-dibromo-4-(2,3-dibromopropyloxy)}phenyl]propane is preferred.

The purification method of the present invention comprises depositing a high-purity solid bromine compound from the crude solution containing the bromine compound represented by the above general formula (1). The crude solution contains a bromine compound formed by an addition reaction of bromine ($Br_2$). This addition reaction is a reaction for brominating the unsaturated bromine compound represented by the following general formula (2), and the purification method of the present invention is advantageously used for the solution obtained by this reaction.

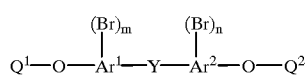

(2)

wherein $Ar^1$, $Ar^2$, Y, m and n are the same as defined in the above general formula (1), and $Q^1$ and $Q^2$ are the same or different and each a hydrocarbon group having 1 or 2 unsaturated groups and 2 to 5 carbon atoms.

In the above general formula (2), $Ar^1$, $Ar^2$, Y, m and n are preferably the same as defined in the above general formula (1). Illustrative examples of the hydrocarbon group represented by $Q^1$ and $Q^2$ include vinyl group, allyl group and isobutenyl group. Of these, allyl group is preferred.

Illustrative examples of the unsaturated bromine compound represented by the above general formula (2) include 2,2-bis{(3,5-dibromo-4-allyloxy)phenyl}propane, 2,2-bis{(3,5-dibromo-4-isobutenyloxy)phenyl}propane, bis{(3,5-dibromo-4-allyloxy)phenyl}methane, bis{(3,5-dibromo-4-isobutenyloxy)phenyl}methane, (3,3',5,5'-tetrabromo-4,4'-diallyloxy)biphenyl, (3,3',5,5'-tetrabromo-4,4'-divinyloxy)biphenyl, bis{(3,5-dibromo-4-allyloxy)phenyl}sulfone, bis{(3,5-dibromo-4-isobutenyloxy)phenyl}sulfone and the like. Of these, 2,2-bis{(3,5-dibromo-4-allyloxy)phenyl}propane, 2,2-bis{(3,5-dibromo-4-isobutenyloxy)phenyl}propane, bis{(3,5-dibromo-4-allyloxy)phenyl}methane, bis{(3,5-dibromo-4-isobutenyloxy)phenyl}methane, (3,3',5,5'-tetrabromo-4,4'-diallyloxy)biphenyl and (3,3',5,5'-tetrabromo-4,4'-divinyloxy)biphenyl are preferred; 2,2-bis{(3,5-dibromo- 4-allyloxy)phenyl}propane, 2,2-bis{(3,5-dibromo-4-isobutenyloxy)phenyl}propane, bis{(3,5-dibromo-4-allyloxy)phenyl}methane and bis{(3,5-dibromo-4-isobutenyloxy)phenyl}methane are more preferred; and 2,2-bis{(3,5-dibromo-4-allyloxy)phenyl}propane is particularly preferred.

The reaction between the unsaturated bromine compound and bromine is carried out in the presence of a solvent, and the solvent does not have an adverse effect on the reaction and is inactive. The higher the solubility of the solvent for the unsaturated bromine compound the more preferable, but the solvent may be a solvent only part of which is dissolved. The bromine compound produced by the bromination reaction of the unsaturated bromine compound is preferably one that is substantially dissolved in the solvent.

The solvent in the above bromination reaction acts not only as a solvent for carrying out a reaction uniformly but also as a solvent for removing reaction heat from a reaction system effectively. Therefore, a solvent having a boiling point of 0 to 100° C., preferably 20 to 90° C., at normal pressure is advantageous. Particularly when reaction heat is removed substantially by the vaporization heat of a solvent, it is desired that the solvent have a boiling point of 20 to 80° C., preferably 20 to 60° C., at normal pressure.

Illustrative examples of the solvent include hydrocarbon halides such as methylene chloride, chloroform, 1,2-dichloroethane, 1,1-dichloroethane, bromoethane, butylchloride and chloropropane; ether-based hydrocarbon compounds such as diethyl ether, ethyl isopropyl ether, tetrahydrofuran and dioxane; aromatic hydrocarbon compounds such as toluene; and the like. Bromine can be used as the solvent.

Of these solvents, hydrocarbon halides are preferred, and methylene chloride and chloroform are particularly preferred. These solvents may be used alone or in admixture of two or more. These hydrocarbon halides may be used as a mixed solvent with dioxane.

As for the amount of bromine used in the above bromination, the molar ratio of bromine to the unsaturated bromine compound must be sufficient to obtain a desired bromine compound. That is, the number of molecules of bromine per unsaturated group of the unsaturated bromine compound is preferably 1 to 5, more preferably 1.1 to 3.

In the above bromination, bromine itself or a bromine solution is used. A solvent to be used in the bromine solution is the same as the above solvent. In this case, the concentration of bromine is preferably 10 to 90 wt %.

In the above bromination, the unsaturated bromine compound is reacted with bromine by mixing bromine or a bromine solution with a solution of the unsaturated bromine compound dissolved in a solvent which is inactive with bromine. It is preferred to remove the substantial amount of reaction heat of bromination by the vaporization heat of the solvent or bromine during this bromination reaction. The substantial amount of the reaction heat means 80% or more, preferably 85% or more, of the theoretical amount of heat generated by a desired bromination reaction.

The reaction temperature of the bromination reaction is preferably a temperature at which the substantial amount of the reaction heat of bromination is removed by the vaporization heat of bromine or the solvent as described above. The bromination reaction can be carried out not only at normal pressure but also at an increased pressure or a reduced pressure. The reaction temperature can be controlled by operation pressure corresponding to the type (or boiling point) of the used solvent and the amount of bromine. The reaction temperature is generally 0 to 60° C., preferably 5 to 55° C., particularly preferably 10 to 50° C.

The purification method of the present invention is advantageously used to separate a purified bromine compound from the reaction mixture obtained by the above bromination reaction. Since this reaction mixture is obtained as a crude solution containing a bromine compound, the purification treatment of the present invention can be directly applied to this solution. However, since unreacted bromine ($Br_2$) still remains in the above reaction mixture and adversely affects the purification step or recovery step, it is desired to convert it into another compound by subjecting it to a chemical treatment.

This chemical treatment comprises treating the bromine remaining in the reaction mixture with a reducing agent to convert it into hydrobromic acid and neutralizing the hydrobromic acid with an alkaline neutralizing agent. This method is carried out by adding a reducing agent and a neutralizing agent to the above reaction mixture.

The reducing agent used in this treatment method is a reducing agent which is used in an ordinary reduction reaction, as exemplified by sodium hydrogen sulfite, sodium dithionite, sodium sulfite, oxalic acid, hydrogen sulfide, sodium nitrite, potassium nitrite, hydroxyamine sulfate, tin, stannous oxide, hydrazine and the like. Of these, sodium hydrogen sulfite, sodium dithionite, sodium sulfite, oxalic acid and sodium nitrite are preferred. These reducing agents may be used as an aqueous solution. These reducing agents may be used alone or in admixture of two or more.

Illustrative examples of the alkaline neutralizing agent include alkali metal hydroxides, alkali metal carbonates, alkaline earth metal hydroxides, alkaline earth metal carbonates and the like. Specifically, sodium hydroxide, potassium hydroxide, sodium carbonate, potassium carbonate, calcium hydroxide and calcium carbonate are preferred, and sodium hydroxide is particularly preferred. These alkaline neutralizing agents are preferably used as an aqueous solution. These alkaline neutralizing agents may be used alone or in admixture of two or more.

In the above treatment method, the reducing agent is added to the reaction mixture in an amount of 2 moles or more, preferably 2 to 30 moles, more preferably 2.2 to 15 moles, much more preferably 2.5 to 10 moles, based on 1 mol of the residual bromine contained in the reaction mixture. When the amount of the reducing agent to be added is smaller than 2 moles, bromine remains in the mixture with the result that a low-purity bromine compound which is colored brown is obtained disadvantageously. The alkaline neutralizing agent is added to the reaction mixture in an amount of 2 moles or more, preferably 2 to 50 moles, more preferably 2.2 to 30 moles, much more preferably 2.5 to 20 moles, based on 1 mol of the residual bromine contained in the reaction mixture. When the amount of the neutralizing agent to be added is smaller than 2 moles, hydrogen bromide remains in the aqueous solution. This strong acid aqueous solution cannot be discarded directly. Further, part of the hydrogen bromide remains in the mixture, and this readily corrodes a metal and has an irritating smell, which is not preferred from the viewpoint of working environment.

The above reducing agent and the above alkaline neutralizing agent are added to the reaction mixture containing a bromine compound and bromine simultaneously or separately. Although the reducing agent and the neutralizing agent may be added separately or as a mixture, they are preferably added separately because the reducing agent can never cause a secondary reaction because of alkali. As for how to add these agent, it is preferred to add the reducing agent first, followed by the neutralizing agent.

In the treatment method, the reaction mixture containing the reducing agent and the neutralizing agent is mixed to carry out reduction and neutralization reactions smoothly.

The weight ratio of the reaction mixture to a water phase at the time of carrying out the reduction and neutralization reactions is preferably 20:80 to 80:20, more preferably 30:70 to 70:30, particularly preferably 40:60 to 60:40. Within this range, the reduction and neutralization reactions proceed efficiently and bromine is removed in a short period of time. Therefore, water or the solvent is preferably added to the reaction mixture in such an amount that ensures that the weight ratio should fall within the above range before the reduction and neutralization reactions are carried out.

The amount of time required to carry out the reduction and neutralization reactions of bromine contained in the reaction mixture is preferably 2 minutes or more, more preferably 2 to 90 minutes, much more preferably 5 to 60 minutes, particularly preferably 10 to 45 minutes.

The reaction mixture (organic phase) is separated from the water phase by carrying out the above reduction and neutralization treatments, and this organic phase can be used as a crude solution to be purified by the purification method of the present invention.

The crude solution to be purified by the purification method of the present invention preferably contains a bromine compound (1) in an amount of 10 to 80 wt %, preferably 20 to 65 wt %, particularly preferably 25 to 55 wt %.

A solvent forming the crude solution of the bromine compound (1) is a good solvent for the bromine compound (1). The good solvent has a solubility for the bromine compound (1) of $1/100$ g or more of the solvent, preferably $2/100$ g or more of the solvent, at 250° C. Preferred examples of the good solvent include methylene chloride, chloroform, 1,2-dichloroethane, 1,1-dichloroethane, cyclohexanone, ethyl acetate and toluene. They may be used alone or in admixture of two or more. Of these, hydrocarbon halides such as methylene chloride and chloroform are preferred, and methylene chloride is preferred the most.

As described above, the crude solution of the bromine compound (1) can be a solution produced by the above bromination or a reaction mixture derived from the solution. In this case, the solution of a reaction solvent used for the bromination can be used directly or after subjected to a supplementary chemical treatment.

In the purification method of the present invention, it is important to supply the crude solution containing the bromine compound (1) as described above into a slurry containing particles of the bromine compound (1) that satisfies the following requirements (a) and (b) and deposit a bromine compound contained in the crude solution. The solvent contained in the slurry is a mixed solvent of a good solvent and a poor solvent for a bromine compound as described in (b).

(a) The slurry should contain the particles of the bromine compound in an amount of 10 to 50 wt %, preferably 15 to 40 wt %.

(b) The solvent contained in the slurry should be a mixed solvent of a good solvent and a poor solvent for a bromine compound and should have a solubility for the bromine compound of 0.1 to 5 g/100 g of solvent, preferably 0.5 to 4 g/100 g of solvent.

The purification method of the present invention is to supply the crude solution containing the bromine compound into a deposition vessel while the above requirements (a) and (b) are satisfied. It is considered that the particles of the bromine compound forming the slurry serve as seed crystals for the bromine compound to be separated out from the solution while the composition of the mixed solvent promotes the deposition of the bromine compound, suppresses the deposition of impurities and keeps them dissolved in the solution.

To carry out the method of the present invention, the crude solution is supplied into the deposition vessel, and a poor solvent and the particles of the bromine compound (seed crystals) or a mixture solution thereof is further supplied to the vessel while the requirements (a) and (b) are satisfied. At this point, a good solvent or a mixed solvent of a good solvent and a poor solvent can be supplied as required.

The poor solvent for a bromine compound has a solubility for the bromine compound (1) of 0.08/100 g or less of solvent, preferably 0.05/100 g or less of solvent, particularly preferably 0.01/100 g or less of solvent. The term "solubility" means a value measured at a temperature of 25° C. The solubilities of the good solvent and the mixed solvent also mean values measured at 25° C.

Specific examples of the poor solvent include water; saturated monovalent alcohols having 1 to 5 carbon atoms such as methanol, ethanol and i-propanol; ethylene glycol; glycerin; diethyl ether; dipropyl ether; diisopropyl ether; saturated hydrocarbons having 5 to 10 carbon atoms such as n-pentane, n-hexane and n-octane; and the like. Water, methanol, ethanol, i-propanol and diisopropyl ether are preferred; water, methanol, ethanol and i-propanol are more preferred; and methanol is particularly preferred. These poor solvents may be used alone or in admixture of two or more.

The operation of depositing a bromine compound in the purification method of the present invention requires neither cooling nor heating, but it is advantageously carried out generally at a temperature of 5 to 50° C., preferably 10 to 45° C.

The particles of the bromine compound as a slurry have an average particle diameter of 0.1 to 0.8 mm, preferably 0.2 to 0.7 mm.

Although the purification method of the present invention may be carried out by either a batch or continuous process, it is made suitable for use with a continuous process. Therefore, the continuous process is industrially advantageous.

The batch process and the continuous process will be explained in detail hereinafter. To simplify explanation, the following terms are defined as follows.

crude solution: a crude solution containing a bromine compound
seed crystals: particles of the bromine compound
good solvent: a good solvent for the bromine compound
poor solvent: a poor solvent for the bromine compound
mixed solvent: a mixed solvent of the good solvent and the poor solvent
vessel: a vessel equipped with a stirrer for depositing the bromine compound A description is first given of the operation of purification in accordance with the batch process. The batch process can be further classified into the following subprocesses (1) to (4).

(1) a subprocess for supplying only the crude solution or both the crude solution and the poor solvent into a vessel filled with a slurry containing the seed crystals and the mixed solvent (2) a subprocess for supplying (i) the crude solution and (ii) the slurry containing the seed crystals and the mixed solvent into the vessel (3) a subprocess for supplying (i) the crude solution, (ii) the slurry containing the seed crystals and the mixed solvent and (iii) the poor solvent into the vessel (4) a subprocess for supplying (i) the crude solution, (ii) the slurry containing the seed crystals and the poor solvent and (iii) the poor solvent into the vessel These steps (1) to (4) are for explaining the batch process, and slight modifications are free to be made. For example, in the subprocess (1), a good solvent may be further supplied into the vessel, or the slurry containing the seed crystals and the mixed solvent may be supplied into the vessel. In the subprocesses (1) to (4), the composition and supply speed of each flow may not be fixed and may be changed.

Further, in the batch process, there may be used a subprocess in which part of the slurry in the vessel may be extracted and recycled to the vessel.

In the subprocesses (1) to (4), it is desirable that the slurry in the vessel be fully mixed by agitation or the like in order to improve a deposition effect and obtain a high-purity bromine compound.

A description is subsequently given of the continuous process. The continuous process comprises depositing a bromine compound in the vessel to extract the slurry from the vessel continuously or intermittently while the crude solution is continuously supplied into the vessel.

According to the present invention, the following method is proposed to carry out the method of the present invention continuously.

That is, according to the present invention, there is provided a method for continuously purifying a bromine compound by depositing the bromine compound represented by the above general formula (1) as solid particles from a crude solution containing the bromine compound, wherein (i) the crude solution and a poor solvent for the bromine compound are continuously supplied into a vessel containing the slurry that contains the particles of the bromine compound to deposit the bromine compound in the slurry under agitation;

(ii) the concentration of the particles of the bromine compound in the slurry contained in the vessel is maintained at 10 to 50 wt %;

(iii) the solvent in the slurry contained in the vessel is a mixed solvent of a good solvent and a poor solvent for the bromine compound and the solubility of the bromine compound in the mixed solvent is maintained at 0.1 to 5 g/100 g of solvent; and (iv) the slurry is continuously extracted from the vessel and the solid particles of the bromine compound are separated from the slurry.

To carry out the above continuous method, the following modifications may be made.

(a) The good solvent may be supplied into the vessel as a supplement.

(b) Part of the slurry extracted from the vessel may be recycled to the vessel.

(c) The slurry extracted from the vessel may be separated into the wet cake of the bromine compound and a mother liquor by solid-liquid separation, and part of the mother liquor may be supplied into the vessel. The recycling of the mother liquor is preferred because it improves the recovery of the bromine compound of interest.

The above modifications may be made independently or in combination as desired.

The particles of a high-purity bromine compound of interest can be obtained by separating the slurry containing the particles of the bromine compound obtained by the above batch process or the continuous process into a wet cake and a mother liquor by centrifugation or filtration and drying the wet cake. The dried wet cake may further be ground in some cases.

The particles of the bromine compound obtained in the present invention preferably have a weight-based average particle diameter of 0.1 to 0.9 mm, more preferably 0.1 to 0.8 mm, the most preferably 0.2 to 0.7 mm. When the average particle diameter is smaller than 0.1 mm, handling properties deteriorate and a working environment is worsen due to the scattering of dust, disadvantageously. On the other hand, when the average particle diameter is larger than 0.9 mm, the dispersibility of the bromine compound used as a flame retardant into a resin degrades, disadvantageously.

According to the purification method of the present invention, a high-purity bromine compound can be obtained industrially advantageously. This bromine compound is useful as a flame retardant for resins, particularly as a high-quality flame retardant for ABS resins, polystyrene resins and polyolefin resins.

It has been found that a high-purity bromine compound having extremely high quality can be obtained according to conditions favorable to the method of the present invention. That is, since the bromine compound is obtained by a bromination reaction, it contains not a few bromine ions. The concentration of bromine ions in commercially available bromine compounds is about 10 ppm or more at minimum and 20 ppm or more in most cases. When a bromine compound having a high concentration of bromine ions is added to a resin as a flame retardant, it causes the decomposition, modification and coloration of the resin and further the corrosion of a molding machine.

However, under the favorable conditions of the present invention, it is possible to provide a high-quality bromine compound having a bromine ion concentration of 5 ppm or less, preferably 4 ppm or less.

It has also been found that the particles of the bromine compound obtained by the purification method of the present invention have a shape characteristic different from that of the prior art. This shape characteristic is that the particles show extremely small compressibility when compressed. When the shape characteristic of the particles is expressed by the compressibility (%) represented by the following equation, the particles of the bromine compound of the present invention have a compressibility of 0.1 to 20% preferably 1 to 15%.

$$\text{compressibility } (\%) = (P-A)/P \times 100$$

wherein A is a loose apparent density (g/cm$^3$) of the particles and P is an hard apparent density (g/cm$^3$) of the particles.

Since the bromine compound obtained by the present invention has a high purity and a low compressibility of 0.1 to 20%, it has such advantages that the deformation and powdering of its particles by storage, transfer and blending operations hardly occur and that it is easy to handle.

The bromine compound obtained by the purification method of the present invention generally has a purity of 94 wt % or more, preferably 95 wt % or more, particularly preferably 96 wt % or more. Thus, the bromine compound has an extremely high purity and extremely small contents of unfavorable impurities.

Further, the particles of the bromine compound obtained by the present invention have an inclination angle, measured by a method which will be described hereinafter, of 5 to 70°, preferably 5 to 45°. This small inclination angle means that the blocking of the particles hardly occurs and that the particles are very easy to handle.

EXAMPLES

The following examples are given to further illustrate the present invention. Purity, average particle diameter, solubility, the proportion of crystals contained in the slurry, and specific gravity were measured in accordance with the following methods.

(1) Analysis of Purity

The purity was measured by a high-performance liquid chromatography ("HPLC": SCL-6B of Shimadzu Corporation) in accordance with a method for detecting the absorption of 280 nm.

(2) Average Particle Diameter

A sample was screened using 200-mesh, 100-mesh, 60-mesh, 20-mesh, 16-mesh, 10-mesh, 5-mesh and 3.5-mesh screens to form a cumulative particle size distribution graph based on weight so as to obtain an average particle diameter. As for particles having an average particle diameter of 0.1 mm or less, since they cannot be screened by any of the above screens, an average particle diameter was obtained from a cumulative particle size distribution graph based on the weight obtained by using the Coalter LS230 particle size distribution measuring instrument.

(3) Solubility

An excess of sample powders was dissolved in a predetermined solvent at a predetermined temperature and saturated completely at that temperature. Thereafter, a predetermined amount of this solution was measured accurately, the solvent was completely removed from the solution, and the weight of the residue was measured to calculate the solubility of the sample in the solvent.

(4) Proportion of Crystals in Slurry

A predetermined amount of slurry was filtered to obtain crystals, which were then dried at 80° C. and 5 mmHg for 3 hours. The weight of the crystals was measured to calculate the weight ratio of the crystals to the slurry.

(5) Specific Gravity

This was measured at 20° C. using a glass pycnometer.

(6) Compressibility

A TBA-BE particulate sample was slowly added from above to a stainless cylindrical vessel having a diameter of 50 mm and a volume of 100 cm$^3$ and was leveled with the brim. The weight X (g) of the TBA-BE particulate sample in the vessel was measured to obtain loose apparent density A (g/cm$^3$) {=X (g)/100 (cm$^3$)}. Thereafter, an accessory frame (a diameter of 50 mm and a height of 40 mm) having the same diameter as that of the vessel was attached to the vessel, and the TBA-BE particulate sample was further added thereto. After tapping was carried out 180 times at intervals of 1 second using the powder tester of Hosokawa Micron Co., Ltd. at a drop height of 18 mm, the frame was removed and the TBA-BE particulate sample was leveled with the brim of the cylindrical vessel. At this point, the weight Y (g) of the TBA-BE particulate sample in the cylindrical vessel was measured to obtain hard apparent density P (g/cm$^3$) {=Y (g)/100 (cm$^3$)}. Compressibility was calculated from the following equation (1).

$$\text{compressibility } (\%) = 100 \, (P-A)/P \quad (1)$$

(7) Long-term Storage Stability Test

10 Grams of a TBA-BE particulate sample was charged into a cylindrical cell having an inner diameter of 20 mm and stored in a hot-air circulating drier kept at 40° C. for 3 months with a load of 0.4 kgf applied to the particulate layer from the top of the cell. After three months, the degree of blocking of the particulate sample taken out of the cell was observed. Long-term storage stability was evaluated as ⊙ when the particulate sample did not change so much in appearance before and after the test, ○ when the particulate sample became solid but easily returned to its original state by touching it with a hand, and X when the particulate layer became hard and was not broken by touching it with a hand.

(8) Concentration of Bromine Ions

1 Gram of a sample was dissolved in 10 ml of methylene chloride, and 10 ml of water was added to this solution and mixed thoroughly. The concentration of bromine ions extracted into water was measured by ion chromatography (Series 2000i/SP of DIONEX Co., Ltd.) to calculate the concentration of the bromine ions in the sample.

Referential Example A 2,2-bis[{3,5-dibromo-4-(2,3-dibromopropyloxy)}phenyl]propane having a purity of 93% was recrystallized using ethyl acetate, whereby crystals of 2,2-bis[{3,5-dibromo-4-(2,3-dibromopropyloxy)}phenyl]propane having a purity of 94% and an average particle diameter of 0.2 mm were obtained (to be referred to as "seed crystals A" hereinafter). Thereafter, recrystallization was carried out two more time in the same manner as described above to give crystals of 2,2-bis[{3,5-dibromo-4-(2,3-dibromopropyloxy)}phenyl]propane having a purity of 99% and an average particle diameter of 0.2 mm (to be referred to as "seed crystals B" hereinafter).

Referential Example B

100 Grams (0.160 mole) of commercially available TBA-AE (FG-3200 of Teijin Kasei Co., Ltd.) and 150 g of methylene chloride were charged into a flask equipped with a thermometer, stirrer and reflux cooling tube, and the mixture was molten at 20° C. After 54 g (0.338 mole) of bromine was added dropwise to this solution over 1 hour, the resulting solution was stirred for 1 hour at the same temperature to complete the addition reaction of bromine.

Thereafter, the excessive bromine contained in the solution was reduced with 30 ml of a 25 wt % aqueous solution of sodium hydrogen sulfite to produce hydrogen bromide, which was then neutralized with 11 ml of a 24 wt % aqueous solution of sodium hydroxide and washed with 150 ml of purified water to give a 50 wt % methylene chloride solution of TBA-BE. A methylene chloride solution was added to this solution to prepare a 33 wt % methylene chloride solution. When part of this solution was extracted and concentrated, the purity of its solid content was 90%.

Referential Example C 1,000 Grams (1.60 moles) of 2,2-bis{(3,5-dibromo-4-allyloxy)phenyl}propane (raw material (1)) were dissolved in 1,703 g (20.0 moles) of methylene chloride. This solution had a specific gravity of 1.46, and contained 160 ppm of water when measured by a Karl Fischer's method.

This solution was added to a glass reactor equipped with a stirrer, capacitor and thermometer from its input port at a rate of $5.3 \times 10^{-3}$ l/min and bromine from the input port at a rate of $0.58 \times 10^{-3}$ l/min continuously (molar ratio of bromine to the raw material (1) was 2.45). The solution mixed in the reactor generated heat due to the reaction heat of bromination, and vapor generated was refluxed to the reactor by the fully cooled capacitor. About 20 minutes from the beginning of adding the solution of the raw material (1) and bromine, a reaction solution began to be output from an output port and continued to be output thereafter (residence time of 20.4 minutes). Part of the reaction solution in the reactor (120 ml) had been recycled to the reactor at a rate of 0.03 l/min using a pump since it began to be output.

The excessive bromine contained in the reaction solution output from the reactor was reduced with an aqueous solution of soda disulfide (about 15 wt %) to produce hydrogen bromine, which was then neutralized with an aqueous solution of sodium hydroxide. Thereafter, 1,000 g of ion exchange water was added to this solution, and the resulting solution was stirred to separate a methylene chloride layer. The purity of the solid 2,2-bis{3,5-dibromo-4-(2,3-dibromopropyloxy)phenyl}propane recovered from this methylene chloride solution was 94.2%. The concentration of the bromine compound in the methylene chloride phase was 50.2%.

Example 1

2.5 kilograms of methylene chloride, 2.5 kg of methanol and 2.5 kg of the seed crystals B obtained in the Referential Example A were charged into the flask shown in FIG. 1 and mixed together (this solid-liquid mixture had a specific gravity of 1.15 and a volume of 6.5 liters).

A 50 wt % methylene chloride solution of 2,2-bis[{3,5-dibromo-4-(2,3-dibromopropyloxy)}phenyl]propane having a purity of 90% obtained in Referential Example B, methanol, and a solid-liquid mixture containing methylene chloride and methanol in a weight ratio of 50:50 as well as 33 wt % of the seed crystals B obtained in the Referential Example A were continuously added to the flask for 8 hours under agitation at a temperature of 25° C. and at rates of 0.05 l/min, 0.05 l/min and 0.03 l/min by a quantitative pump, respectively. 10 minutes after the beginning of the addition, the slurry in the flask was removed from an extraction nozzle 8 at a rate of 0.13 l/min while circulated at a rate of 3.5 l/min by a pump 6 (residence time was 60 minutes). The slurry that had been removed in 7 to 8 hours since the start of the addition was filtered and dried at 80° C. and a reduced pressure of 5 mmHg for 3 hours to obtain crystals of 2,2-bis[{3,5-dibromo-4-(2,3-dibromopropyloxy}phenyl]propane. The obtained crystals had a purity of 96% and an average particle diameter of 0.4 mm, and the recovery was 96%.

The weight ratio of methylene chloride to methanol in the slurry was 50:50 (solubility of 2,2-bis[{3,5-dibromo-4-(2,3-dibromopropyloxy)}phenyl]propane (may be abbreviated as "TBA-BEN" hereinafter) at 25° C. was 0.7 wt %), and the proportion of the TBA-BE crystals in the slurry was 33 wt %.

Example 2

2.5 kilograms of methylene chloride, 2.5 kg of methanol and 2.5 kg of the seed crystals B obtained in the Referential Example A were charged into the flask shown in FIG. 1 and mixed together (this solid-liquid mixture had a specific gravity of 1.15 and a volume of 6.5 liters).

A 50 wt % methylene chloride solution of 2,2-bis[{3,5-dibromo-4-(2,3-dibromopropyloxy)}phenyl]propane having a purity of 90% obtained in Referential Example B and methanol were continuously added to the flask for 8 hours under agitation at a temperature of 25° C. and at rates of 0.05 l/min and 0.05 l/min by a quantitative pump, respectively. 10 minutes after the beginning of the addition, the slurry in the flask was removed from an extraction nozzle 8 at a rate of 0.1 l/min while circulated at a rate of 3.5 l/min by a pump 6 (residence time was 75 minutes). The slurry that had been removed in 7 to 8 hours since the beginning of the addition was filtered and dried at 80° C. and a reduced pressure of 5 mmHg for 3 hours to obtain crystals of 2,2-bis[{3,5-dibromo- 4-(2,3-dibromopropyloxy)}phenyl]propane. The obtained crystals had a purity of 96% and an average particle diameter of 0.2 mm, and the recovery was 95%.

The weight ratio of methylene chloride to methanol in the slurry was 50:50 (solubility of TBA-BE at 25° C. was 0.7 wt %), and the proportion of the TBA-BE crystals in the slurry was 33 wt %.

Example 3

A 50 wt % methylene chloride solution of 2,2-bis[{3,5-dibromo-4-(2,3-dibromopropyloxy)}phenyl]propane having a purity of 90% obtained in Referential Example B, methanol and a solid-liquid mixture containing methanol and methylene chloride in a weight ratio of 50:50 as well as 33 wt % of the seed crystals B obtained in the Referential Example A were continuously added to the flask shown in FIG. 1 for 8 hours under agitation at a temperature of 25° C. and at rates of 0.05 l/min, 0.05 l/min and 0.03 l/min by a quantitative pump, respectively. 20 minutes after the beginning of the addition, the slurry in the flask was removed from an extraction nozzle 8 at a rate of 0.13 l/min while circulated at a rate of 3.5 l/min by a pump 6 (residence time was 20 minutes). The slurry that had been removed in 7 to 8 hours since the beginning of the addition was filtered and dried at 80° C. and a reduced pressure of 5 mmHg for 3 hours to obtain crystals of 2,2-bis[{3,5-dibromo-4-(2,3-dibromopropyloxy)}phenyl]propane. The obtained crystals had a purity of 96% and an average particle diameter of 0.4 mm, and the recovery was 96%.

The weight ratio of methylene chloride to methanol in the slurry was 50:50 (solubility of TBA-BE at 25° C. was 0.7 wt %), and the proportion of the TBA-BE crystals in the slurry was 33 wt %.

Example 4

The procedure of Example 1 was repeated except that the crystallization temperature was changed from 25° C. to 40° C. and the seed crystals A were used in place of the seed crystals B to obtain crystals of 2,2-bis[{3,5-dibromo-4-(2,3-dibromopropyloxy)}phenyl]propane. The obtained crystals had a purity of 96% and an average particle diameter of 0.2 mm, and the recovery was 94%.

The weight ratio of methylene chloride to methanol in the slurry was 50:50 (solubility of TBA-BE at 40° C. was 1.6 wt %), and the proportion of the TBA-BE crystals in the slurry was 33 wt %.

Example 5

2 kilograms of methylene chloride, 3 kg of methanol and 2.5 kg of the seed crystals B obtained in the Referential Example A were charged into the flask shown in FIG. 1 and mixed together (this solid-liquid mixture had a specific gravity of 1.10 and a volume of 6.8 liters).

A 50 wt % methylene chloride solution of 2,2-bis[{3,5-dibromo-4-(2,3-dibromopropyloxy)}phenyl]propane having a purity of 90% obtained in Referential Example B and methanol were continuously added to the flask for 8 hours under agitation at a temperature of 25° C. and at rates of 0.02 l/min and 0.03 l/min by a quantitative pump, respectively. 10 minutes after the beginning of the addition, the slurry in the flask was removed from an extraction nozzle 8 at a rate of 0.05 l/min while circulated at a rate of 3.5 l/min by a pump 6 (residence time was 146 minutes). The slurry that had been removed in 7 to 8 hours since the beginning of the addition was filtered and dried at 80° C. and a reduced pressure of 5 mmHg for 3 hours to obtain crystals of 2,2-bis[{3,5-dibromo-4-(2,3-dibromopropyloxy)}phenyl]propane. The obtained crystals had a purity of 95% and an average particle diameter of 0.3 mm, and the recovery was 96%.

The weight ratio of methylene chloride to methanol in the slurry was 40:60 (solubility of TBA-BE at 25° C. was 0.2 wt %) and the proportion of the TBA-BE crystals in the slurry was 28 to 33 wt %.

Example 6

1.5 kilograms of methylene chloride, 3.5 kg of methanol and 2.5 kg of the seed crystals B obtained in the Referential Example A were charged into the flask shown in FIG. 1 and mixed together (this solid-liquid mixture had a specific gravity of 1.04 and a volume of 7.2 liters).

A 50 wt % methylene chloride solution of 2,2-bis[{3,5-dibromo-4-(2,3-dibromopropyloxy)}phenyl]propane having a purity of 90% obtained in Referential Example B and methanol were continuously added to the flask for 8 hours under agitation at a temperature of 400° C. and at rates of 0.015 l/min and 0.035 l/min by a quantitative pump, respectively. 10 minutes after the beginning of the addition, the slurry in the flask was removed from an extraction nozzle 8 at a rate of 0.05 l/min while circulated at a rate of 3.5 l/min by a pump 6 (residence time was 154 minutes). The slurry that had been removed in 7 to 8 hours since the beginning of the addition was filtered and dried at 80° C. and a reduced pressure of 5 mmHg for 3 hours to obtain crystals of 2,2-bis[{3,5-dibromo-4-(2,3-dibromopropyloxy)}phenyl]propane. The obtained crystals had a purity of 95% and an average particle diameter of 0.4 mm, and the recovery was 97%.

The weight ratio of methylene chloride to methanol in the slurry was 30:70 (solubility of TBA-BE at 40° C. was 0.1 wt %), and the proportion of the TBA-BE crystals in the slurry was 22 to 33 wt %.

Example 7

3 kilograms of methylene chloride, 2 kg of methanol and 2.5 kg of the seed crystals B obtained in the Referential Example A were charged into the flask shown in FIG. 1 and mixed together (this solid-liquid mixture had a specific gravity of 1.20 and a volume of 6.3 liters).

A 50 wt % methylene chloride solution of 2,2-bis[{3,5-dibromo-4-(2,3-dibromopropyloxy)}phenyl]propane having a purity of 90% obtained in Referential Example B and methanol were continuously added to the flask for 8 hours under agitation at a temperature of 35° C. and at rates of 0.06 l/min and 0.04 l/min by a quantitative pump, respectively. 10 minutes after the beginning of the addition, the slurry in the flask was removed from an extraction nozzle 8 at a rate of 0.1 l/min while circulated at a rate of 3.5 l/min by a pump 6 (residence time was 73 minutes). The slurry that had been removed in 7 to 8 hours since the beginning of the addition was filtered and dried at 80° C. and a reduced pressure of 5 mmHg for 3 hours to give crystals of 2,2-bis[{3,5-dibromo-4-(2,3-dibromopropyloxy)}phenyl]propane. The obtained crystals had a purity of 97% and an average particle diameter of 0.2 mm, and the recovery was 84%.

The weight ratio of methylene chloride to methanol in the slurry was 60:40 (solubility of TBA-BE at 35° C. was 4.0 wt %), and the proportion of the TBA-BE crystals in the slurry was 33 wt %.

Example 8

Crystals of 2,2-bis[{3,5-dibromo-4-(2,3-dibromopropyloxy)}phenyl]propane were obtained in the same manner as in Example 1 except that 1,2-dichloroethane was used in place of methylene chloride. The obtained crystals had a purity of 94% and an average particle diameter of 0.3 mm, and the recovery was 95%.

The weight ratio of 1,2-dichloroethane to methanol in the slurry was 50:50 (solubility of TBA-BE at 25° C. was 0.5 wt %), and the proportion of the TBA-BE crystals in the slurry was 33 wt %.

Example 9

2.5 kilograms of toluene, 2.5 kg of methanol and 2.5 kg of the seed crystals B obtained in the Referential Example A were charged into the flask shown in FIG. 1 and mixed together (this solid-liquid mixture had a specific gravity of 0.92 and a volume of 8.2 liters).

A 50 wt % toluene solution of 2,2-bis[{3,5-dibromo-4-(2,3-dibromopropyloxy)}phenyl]propane having a purity of 90% obtained in Referential Example B and methanol were continuously added to the flask for 8 hours under agitation at a temperature of 35° C. and at rates of 0.08 l/min and 0.05 l/min by a quantitative pump, respectively. 10 minutes after the beginning of the addition, the slurry in the flask was removed from an extraction nozzle 8 at a rate of 0.13 l/min while circulated at a rate of 3.5 l/min by a pump 6 (residence time was 73 minutes). The slurry that had been removed in 7 to 8 hours since the start of the addition was filtered and dried at 80° C and a reduced pressure of 5 mmHg for 3 hours to obtain crystals of 2,2-bis[{3,5-dibromo-4-(2,3-dibromopropyloxy)}phenyl]propane. The obtained crystals had a purity of 94% and an average particle diameter of 0.3 mm, and the recovery was 94%.

The weight ratio of toluene to methanol in the slurry was 50:50 (solubility of TBA-BE at 35° C. was 1.4 wt %), and the proportion of the TBA-BE crystals in the slurry was 33 wt %.

Example 10

2.5 kilograms of ethyl acetate, 2.5 kg of diisopropyl ether and 2.5 kg of the seed crystals B obtained in the Referential Example A were charged into the flask shown in FIG. 1 and mixed together (this solid-liquid mixture had a specific gravity of 0.82 and a volume of 9.1 liters).

A 50 wt % ethyl acetate solution of 2,2-bis[{3,5-dibromo-4-(2,3-dibromopropyloxy)}phenyl]propane having a purity of 90% obtained in Referential Example B and diisopropyl ether were continuously added to the flask for 8 hours under agitation at a temperature of 40° C. and at rates of 0.07 l/min and 0.05 l/min by a quantitative pump, respectively. 10 minutes after the beginning of the addition, the slurry in the flask was removed from an extraction nozzle 8 at a rate of 0.12 l/min while circulated at a rate of 3.5 l/min by a pump 6 (residence time was 86 minutes). The slurry that had been removed in 7 to 8 hours since the beginning of the addition was filtered and dried at 80° C. and a reduced pressure of 5 mmHg for 3 hours to obtain crystals of 2,2-bis[{3,5-dibromo-4-(2,3-dibromopropyloxy)}phenyl]propane. The obtained crystals had a purity of 94% and an average particle diameter of 0.3 mm, and the recovery was 95%.

The weight ratio of ethyl acetate to diisopropyl ether in the slurry was 50:50 (solubility of TBA-BE at 40° C. was 1.0 wt %), and the proportion of the TBA-BE crystals in the slurry was 33 wt %.

Example 11

A solid-liquid mixture comprising 67 g of methylene chloride, 67 g of methanol and 30 g of the seed crystals B obtained in the Referential Example A, 225 g of a 50 wt % methylene chloride solution of 2,2-bis[{3,5-dibromo-4-(2,3-dibromopropyloxy)}phenyl]propane having a purity of 90% obtained in Referential Example B, and 113 g of methanol were continuously added for 30 minutes to a 1-liter four-necked flask equipped with a thermometer, stirrer and dropping funnel under agitation from the dropping funnel at a temperature of 250° C., respectively. After the addition was completed, the slurry was further stirred for 30 minutes. Thereafter, the slurry was filtered and dried at 80° C. and a reduced pressure of 5 mmHg for 3 hours to obtain crystals of 2,2-bis[{3,5-dibromo-4-(2,3-dibromopropyloxy)}phenyl]propane. The obtained crystals had a purity of 96% and an average particle diameter of 0.5 mm, and the recovery was 95%.

The weight ratio of methylene chloride to methanol in the slurry was 50:50 (solubility of TBA-BE at 25° C. was 0.7 wt %), and the proportion of the TBA-BE crystals in the slurry was 28 wt %.

Example 12

A solid-liquid mixture comprising 67 g of methylene chloride, 67 g of methanol and 30 g of the seed crystals B obtained in the Referential Example A was charged into a 1-liter four-necked flask equipped with a thermometer, stirrer and dropping funnel.

225 Grams of a 50 wt % methylene chloride solution of 2,2-bis[{3,5-dibromo-4-( 2,3,-dibromopropyloxy)}phenyl] propane having a purity of 90% obtained in Referential Example B and 113 g of methanol were continuously added for 30 minutes from the dropping funnel to the flask under agitation at a temperature of 25° C. After the addition was completed, the slurry was further stirred for 30 minutes. Thereafter, the slurry was filtered and dried at 80° C. and a reduced pressure of 5 mmHg for 3 hours to obtain crystals of 2,2-bis[{3,5-dibromo-4-(2,3-dibromopropyloxy)}phenyl]propane. The obtained crystals had a purity of 95% and an average particle diameter of 0.4 mm, and the recovery was 95%.

The weight ratio of methylene chloride to methanol in the slurry was 50:50 (solubility of TBA-BE at 25° C. was 0.7 wt %), and the proportion of the TBA-BE crystals in the slurry was 18 to 28 wt %.

Example 13

A solid-liquid mixture comprising 67 g of methanol and 30 g of the seed crystals B obtained in the Referential Example A, 359 g of a 50 wt % methylene chloride solution of 2,2-bis[{3,5-dibromo-4-(2,3-dibromopropyloxy)}phenyl]propane having a purity of 90% obtained in Referential Example B, and 113 g of methanol were continuously added for 30 minutes to a 1-liter four-necked flask equipped with a thermometer, stirrer and dropping funnel under agitation from the dropping funnel at a temperature of 25° C. After the addition was completed, the slurry was further stirred for 30 minutes. Thereafter, the slurry was filtered and dried at 80° C. and a reduced pressure of 5 mmHg for 3 hours to obtain crystals of 2,2-bis[{3,5-dibromo-4-(2,3-dibromopropyloxy)}phenyl]propane. The obtained crystals ad a purity of 94% and an average particle diameter of 0.5 mm, and the recovery was 95%.

The weight ratio of methylene chloride to methanol in the slurry was 50:50 (solubility of TBA-BE at 25° C. was 0.7 wt %), and the proportion of the TBA-BE crystals in the slurry was 37 wt %.

Example 14

A solid-liquid mixture comprising 60 g of methylene chloride, 120 g of methanol and 20 g of the seed crystals B obtained in the Referential Example A, and 120 g of a 50 wt % methylene chloride solution of 2,2-bis[{3,5-dibromo-4-(2,3-dibromopropyloxy)}phenyl]propane having a purity of 90% obtained in Referential Example B were continuously added for 30 minutes to a 1-liter four-necked flask equipped with a thermometer, stirrer and dropping funnel under agitation from the dropping funnel at a temperature of 25° C. After the addition was completed, the slurry was further stirred for 30 minutes. Thereafter, the slurry was filtered and dried at 80° C. and a reduced pressure of 5 mmHg for 3 hours to give crystals of 2,2-bis[{3,5-dibromo-4-(2,3-dibromopropyloxy)}phenyl]propane. The obtained crystals had a purity of 95% and an average particle diameter of 0.5 mm, and the recovery was 95%.

The weight ratio of methylene chloride to methanol in the slurry was 50:50 (solubility of TBA-BE at 25° C. was 0.7 wt %), and the proportion of the TBA-BE crystals in the slurry was 25 wt %.

Comparative Example 1

240 Grams of methanol and 20 g of the seed crystals B obtained in the Referential Example A were charged into a flask equipped with a thermometer, stirrer and reflux tube and mixed together. 120 Grams of a 50 wt % methylene chloride solution of 2,2-bis[{3,5-dibromo-4-( 2,3,-dibromopropyloxy}phenyl]propane having a purity of 90% obtained in Referential Example B were added in 30 minutes from a dropping funnel to the flask under agitation at a temperature of 25° C. After the addition was completed, agitation was continued for another 30 minutes. Thereafter, deposited powders were filtered to obtain powders of 2,2-bis[{3,5-dibromo-4-(2,3-dibromopropyloxy)}phenyl] propane. The powders were dried at 80° C. and a reduced pressure of 5 mmHg for 3 hours. The powders, however, were formed into large blocks by adhering to one another during this drying step and were also partially colored. This bromine compound had a purity of 92%, and the recovery was 96%.

The weight ratio of methylene chloride to methanol in the slurry after the addition of the methylene chloride solution was 20:80 (solubility of TBA-BE at 25° C. was 0.02 wt %), and the proportion of the TBA-BE crystals in the slurry was 8 to 20 wt %.

TABLE 1

|  |  | Ex. 1 | Ex. 2 | Ex. 3 | Ex. 4 |
| --- | --- | --- | --- | --- | --- |
| slurry | good solvent | methylene chloride | methylene chloride | methylene chloride | methylene chloride |
|  | poor solvent | methanol | methanol | methanol | methanol |
|  | solubility of bromine compound in solvent (wt %) | 0.7 | 0.7 | 0.7 | 1.6 |
|  | proportion of crystals (wt %) | 33 | 33 | 33 | 33 |
|  | seed crystals | B | B | B | A |
|  | crystallization temperature (° C.) | 25 | 25 | 25 | 40 |
| evaluation | purity (%) | 96 | 96 | 96 | 96 |
|  | average particle diameter (mm) | 0.4 | 0.2 | 0.4 | 0.2 |
|  |  | Ex. 5 | Ex. 6 | Ex. 7 | Ex. 8 |
| slurry | good solvent | methylene chloride | methylene chloride | methylene chloride | 1,2-dichloroethane |
|  | poor solvent | methanol | methanol | methanol | methanol |
|  | solubility of bromine compound in solvent (wt %) | 0.2 | 0.1 | 4.0 | 0.5 |
|  | proportion of crystals (wt %) | 33→28 | 33→22 | 33 | 33 |
|  | seed crystals | B | B | B | B |
|  | crystallization temperature (° C.) | 25 | 40 | 35 | 25 |
| evaluation | purity (%) | 95 | 95 | 97 | 94 |
|  | average particle diameter (mm) | 0.3 | 0.4 | 0.2 | 0.3 |

Ex.: Example

TABLE 2

|  |  | Ex. 9 | Ex. 10 | Ex. 11 | Ex. 12 |
| --- | --- | --- | --- | --- | --- |
| slurry | good solvent | toluene | ethyl acetate | methylene chloride | methylene chloride |
|  | poor solvent | methanol | diisopropyl ether | methanol | methanol |
|  | solubility of bromine compound in solvent (wt %) | 1.4 | 1.0 | 0.7 | 0.7 |
|  | proportion of crystals (wt %) | 33 | 33 | 28 | 18→28 |
|  | seed crystals | B | B | B | B |

TABLE 2-continued

|  |  | | | | |
|---|---|---|---|---|---|
| evaluation | crystallization temperature (° C.) | 35 | 40 | 25 | 25 |
|  | purity (%) | 94 | 94 | 96 | 95 |
|  | average particle diameter (mm) | 0.3 | 0.3 | 0.5 | 0.4 |

|  |  | Ex. 13 | Ex. 14 | Comp. Ex. 1 |
|---|---|---|---|---|
| slurry | good solvent | methylene chloride | methylene chloride | methylene chloride |
|  | poor solvent | methanol | methanol | methanol |
|  | solubility of bromine compound in solvent (wt %) | 0.7 | 0.7 | <0.02 |
|  | proportion of crystals (wt %) | 37 | 25 | 8→20 |
|  | seed crystals | B | B | B |
|  | crystallization temperature (° C.) | 25 | 25 | 25 |
| evaluation | purity (%) | 94 | 95 | 92 |
|  | average particle diameter (mm) | 0.5 | 0.5 | block form |

Ex.: Example
Comp. Ex.: Comparative Example

Example 15

60 Grams of methylene chloride, 120 g of methanol and 20 g of the seed crystals B obtained in Referential Example A were charged into a flask equipped with a thermometer, stirrer and reflux tube and mixed together (the proportion of the seed crystals B in the solid-liquid mixture was 10 wt %). 120 Grams of a 50 wt % methylene chloride solution of 2,2-bis[{3,5-dibromo-4-(2,3-dibromopropyloxy}phenyl]propane having a purity of 90% obtained in Referential Example B was added in 30 minutes from a dropping funnel to this solid-liquid mixture under agitation at a temperature of 25° C. After the addition was completed, agitation was continued for another 30 minutes (at this point, the proportion of the crystals in the slurry was 24 wt % and the weight ratio of methylene chloride to methanol in the slurry was 50:50). Thereafter, the slurry was filtered to extract the crystals, which were then dried at 80° C. and a reduced pressure of 5 mmHg for 3 hours to obtain crystals of 2,2-bis[{3,5-dibromo-4-(2,3-dibromopropyloxy)}phenyl]propane. The obtained crystals had a purity of 95% and an average particle diameter of 0.5 mm, and the recovery was 97%.

Example 16

60 Grams of methylene chloride, 120 g of methanol and 20 g of the seed crystals B obtained in Referential Example A were charged into a flask equipped with a thermometer, stirrer and reflux tube and mixed together (the proportion of the seed crystals B in the solid-liquid mixture was 10 wt %). 120 Grams of a 25 wt % methylene chloride solution of 2,2-bis[{3,5-dibromo-4-(2,3-dibromopropyloxy)}phenyl]propane having a purity of 90% obtained in Referential Example B was added in 30 minutes from a dropping funnel to this solid-liquid mixture under agitation at a temperature of 25° C. After the addition was completed, agitation was continued for another 30 minutes (at this point, the proportion of the crystals in the slurry was 15 wt % and the weight ratio of methylene chloride to methanol in the slurry was 56:44). Thereafter, the slurry was filtered to extract the crystals and dried at 80° C. and a reduced pressure of 5 mmHg for 3 hours to obtain crystals of 2,2-bis[{3,5-dibromo-4-(2,3-dibromopropyloxy)}phenyl]propane. The obtained crystals had a purity of 95% and an average particle diameter of 0.4 mm, and the recovery was 96%.

Example 17

Crystal of 2,2-bis[{3,5-dibromo-4-(2,3-dibromopropyloxy)}phenyl]propane were obtained in the same manner as in Example 15 except that toluene was used in place of methylene chloride. The obtained crystals had a purity of 95% and an average particle diameter of 0.6 mm, and the recovery was 98%.

The conditions and results of above Examples 15 to 17 are shown in Table 3 below.

TABLE 3

|  |  | Ex. 15 | Ex. 16 | Ex. 17 |
|---|---|---|---|---|
| Solid-liquid mixture | good solvent | methylene chloride | methylene chloride | toluene |
|  | poor solvent | methanol | methanol | methanol |
|  | seed crystals | B | B | B |
| solution of bromine compound | solvent | methylene chloride | methylene chloride | toluene |
|  | concentration of bromine compound (wt %) | 50 | 25 | 50 |
| slurry | proportion of crystals (wt %) | 10→24 | 10→15 | 10→24 |
|  | crystallization temperature (° C.) | 25 | 25 | 25 |
| evaluation | purity (%) | 95 | 95 | 95 |
|  | average particle diameter (mm) | 0.5 | 0.4 | 0.6 |

Ex.: Example

Example 18

500 Grams of methylene chloride, 500 g of methanol and 250 g of the seed crystals of TBA-BE having a purity of 99% were charged into the flask shown in FIG. 1.

The 33 wt % methylene chloride solution of TBA-BE obtained in Referential Example B and methanol were continuously added for 8 hours to the flask under agitation at a temperature of 25° C. and at rates of 0.01 l/min and 0.012 l/min by a quantitative pump, respectively. 10 minutes after the beginning of the addition, the slurry in the flask was removed from an extraction nozzle 8 at a rate of 0.022 l/min while circulated at a rate of 0.7 l/min by a pump 6. The slurry that had been removed in 7 to 8 hours from the beginning of the addition was filtered and dried at 80° C. and a reduced pressure of 5 mmHg for 3 hours to obtain crystals of TBA-BE (purity of 94.0%). The recovery was 94%. The obtained crystals were granular powder having an average particle diameter of 0.5 mm and a compressibility of 0.4%. The measurement result of the long-term storage stability of the granular powder by the above evaluation method is shown in Table 4.

The weight ratio of methylene chloride to methanol in the slurry was 50:50 (solubility of TBA-BE at 25° C. was 0.7 wt %), and the proportion of the TBA-BE crystals in the slurry was 20 wt %.

Example 19

500 Grams of methylene chloride, 500 g of methanol and 500 g of the seed crystals of TBA-BE having a purity of 99% were charged into the flask shown in FIG. 1.

The 50 wt % methylene chloride solution of TBA-BE obtained in Referential Example B and methanol were continuously added for 8 hours to the flask under agitation at a temperature of 40° C. and at rates of 0.01 l/min and 0.01 l/min by a quantitative pump, respectively. 10 minutes after the beginning of the addition, the slurry in the flask was removed from an extraction nozzle 8 at a rate of 0.02 l/min while circulated at a rate of 0.7 l/min by a pump 6. The slurry that had been removed in 7 to 8 hours from the beginning of the addition was filtered and dried at 80° C. and a reduced pressure of 5 mmHg for 3 hours to obtain crystals of TBA-BE (purity of 94.3%). The recovery was 95%. The obtained crystals were granular powder having an average particle diameter of 0.2 mm and a compressibility of 2.7%. The measurement result of the long-term storage stability of the granular powder by the above evaluation method is shown in Table 4.

The weight ratio of methylene chloride to methanol in the slurry was 50:50 (solubility of TBA-BE at 25° C. was 0.7 wt %), and the proportion of the TBA-BE crystals in the slurry was 33 wt %.

Example 20

Granular powders were obtained in the same manner as in Example 11 except that 225 g of the methylene chloride solution obtained in Referential Example C were used in place of 225 g of the 50 wt % methylene chloride solution. This solid powders had a purity of 96.8% and properties thereof are shown in Table 4.

Example 21

Granular powders of a bromine compound (purity of 95.7%) were obtained in the same manner as in Example 1 except that the methylene chloride solution obtained in Referential Example C was used in place of the 50 wt % methylene chloride solution. The properties of the powders are shown in Table 4.

Table 4 also shows the properties of the powders of the bromine compound obtained in Comparative Example 1.

TABLE 4

|  | Compressibility (%) | stability under load of 0.4 kgf | residual bromine ion (ppm) | inclination angle (°) |
|---|---|---|---|---|
| Ex. 18 | 0.4 | ⊚ | 3 | 42 |
| Ex. 19 | 2.7 | ⊚ | 5 | 45 |
| Ex. 20 | 0.5 | ⊚ | 4 | 43 |
| Ex. 21 | 0.8 | ⊚ | 4 | 41 |
| Comp. Ex. 1 | 32.3 | ○~X | 25 | >90 |

Ex.: Example
Comp. Ex.: Comparative Example

What is claimed is:

1. A method for continuously purifying a bromine compound having an average particle diameter of 0.1 to 0.9 mm by depositing the bromine compound represented by the following general formula (1) as solid particles from a crude solution containing the bromine compound:

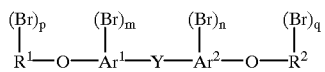

(1)

wherein $Ar^1$ and $Ar^2$ are the same or different and each an aromatic hydrocarbon group having 6 to 10 carbon atoms; Y is an alkylene group having 1 to 3 carbon atoms, single bond, sulfone group or ketone group; $R^1$ and $R^2$ are the same or different and each a hydrocarbon group having 2 to 5 carbon atoms; m and n are the same or different and each an integer of 1 to 4; and p and q are the same or different and each an integer of 2 or 4, wherein (i) the crude solution and a poor solvent for the bromine compound are continuously supplied into a vessel containing the slurry that contains the particles of the bromine compound to deposit the bromine compound in the slurry under agitation;

(ii) the concentration of the particles of the bromine compound in the slurry is maintained at 10 to 50 wt %;

(iii) the solvent in the slurry contained in the vessel is a mixed solvent of a good solvent and a poor solvent for the bromine compound, and the solubility of the bromine compound in the mixed solvent is maintained at 0.1 to 5 g/100 g of the solvent; and (iv) the slurry is continuously extracted from the vessel and the solid particles of the bromine compound are separated from the slurry.

2. The method for continuously purifying a bromine compound according to claim 1, wherein the bromine compound is the compound of the above general formula (1) in which $Ar^1$ and $Ar^2$ are benzene, Y is a methylene group or isopropylidene group, $R^1$ and $R^2$ are an alkyl group having 2 or 3 carbon atoms, m and n are 1 or 2, and p and q are 2.

3. The method for continuously purifying a bromine compound according to claim 1, wherein the concentration of the particles of the bromine compound in the slurry is maintained at 15 to 40 wt %.

4. The method for continuously purifying a bromine compound according to claim 1, wherein the solubility of the bromine compound in the mixed solvent is maintained at 0.5 to 4 g/100 g of the solvent.

5. The method for continuously purifying a bromine compound according to claim 1, wherein the deposition of the bromine compound is carried out at a temperature of 5 to 50° C.

6. The method for continuously purifying a bromine compound according to claim 1, wherein the good solvent has a solubility for the bromine compound of 1/100 g or more of the solvent.

7. The method for continuously purifying a bromine compound according to claim 1, wherein the poor solvent has a solubility for the bromine compound of 0.08/100 g or less of the solvent.

8. The method for continuously purifying a bromine compound according to claim 1, wherein the particles of the bromine compound in the slurry have an average particle diameter of 0.1 to 0.8 mm.

9. The method for continuously purifying a bromine compound according to claim 1, wherein the good solvent is at least one selected from the group consisting of methylene chloride, chloroform, 1,2-dichloroethane, 1,1-dichloroethane, cyclohexanone, ethyl acetate and toluene.

10. The method for continuously purifying a bromine compound according to claim 1, wherein the poor solvent is at least one selected from the group consisting of water, methanol, ethanol, i-propanol and diisopropyl ether.

11. The method for continuously purifying a bromine compound according to claim 1, wherein the crude solution is a solution containing 10 to 80 wt % of the bromine compound.

12. The method for continuously purifying a bromine compound according to claim 1, wherein the crude solution containing the bromine compound represented by the above general formula (1) is a solution derived from a reaction between the unsaturated bromine compound represented by he following general formula (2) and bromine:

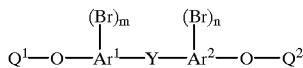

(2)

wherein $Ar^1$, $Ar^2$, Y, m and n are the same as defined in the above general formula (1), and $Q^1$ and $Q^2$ are the same or different and each a hydrocarbon group having 1 or 2 unsaturated groups and 2 to 5 carbon atoms.

13. The method for continuously purifying a bromine compound according to claim 1, wherein part of the slurry extracted continuously from the vessel is recycled to the vessel in the deposition step.

14. The method for continuously purifying a bromine compound according to claim 1, wherein part of the filtrate obtained after the solid particles of the bromine compound are separated from the slurry is recycled to the vessel in the deposition step.

15. A method for purifying a bromine compound by depositing the bromine compound represented by the following general formula (1) as solid particles from a crude solution containing the bromine compound:

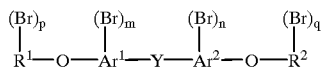

(1)

wherein $Ar^1$ and $Ar^2$ are the same or different and each an aromatic hydrocarbon group having 6 to 10 carbon atoms; Y is a methylene group or isopropylidene group; $R^1$ and $R^2$ are an alkyl group having 2 or 3 atoms; m and n are 1 or 2; and p and q are 2, wherein
  (i) the crude solution is supplied into the slurry containing the particles of the bromine compound to deposit the bromine compound in the slurry under agitation;
  (ii) the concentration of the particles of the bromine compound in the slurry is maintained at 10 to 50 wt %;
  (iii) the solvent contained in the slurry is a mixed solvent of a good solvent and a poor solvent for a bromine compound, the weight ratio of the good solvent to the poor solvent in the slurry is 30:70 to 60:40 and the solubility of the bromine compound in the mixed solvent is maintained at 0.1 to 5 g/100 g of the solvent; and
  (iv) the slurry is extracted to separate the solid particles of the bromine compound from the slurry.

16. The method for purifying a bromine compound according to claim 15, wherein the concentration of the particles of the bromine compound in the slurry is maintained at 15 to 40 wt %.

17. The method for purifying a bromine compound according to claim 16, wherein the solubility of the bromine compound in the mixed solvent is maintained at 0.5 to 4 g/100 g of the solvent.

18. The method for purifying a bromine compound according to claim 15, wherein the good solvent has a solubility for the bromine compound of 1/100 g or more of the solvent and the poor solvent has a solubility for the bromine compound of 0.08/100 g or less of the solvent.

19. The method for purifying a bromine compound according to claim 15, wherein the good solvent is at least one selected from the group consisting of methylene chloride, chloroform, 1,2-dichloroethane, 1,1,-dichloroethane, cyclohexanone, ethyl acetate and toluene and the poor solvent is at least one selected from the group consisting of water, methanol, ethanol, i-propanol and diisopropyl ether.

20. The method for continuously purifying a bromine compound according to claim 1, wherein the purified bromine compound has a bromine ion concentration of 5 ppm or less.

21. The method for continuously purifying a bromine compound according to claim 1, wherein the purified bromine compound contains 94 wt % or more of the bromine compound.

22. A method for continuously purifying a bromine compound to obtain a bromine compound having an average particle diameter of 0.1 to 0.9 mm by depositing the bromine compound represented by the following general formula (1) as solid particles from a crude solution containing the bromine compound:

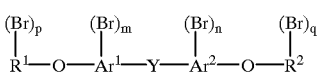

(1)

wherein $Ar^1$ and $Ar^2$ are the same or different and each an aromatic hydrocarbon group having 6 to 10 carbon atoms; Y is a methylene group or isopropylidene group; $R^1$ and $R^2$ are an alkyl group having 2 or 3 atoms; m and n are 1 or 2; and p and q are 2, wherein
  (i) the crude solution and a poor solvent for the bromine compound are continuously supplied into a vessel containing the slurry that contains the particle of the bromine compound to deposit the bromine compound in the slurry under agitation;
  (ii) the concentration of the particles of the bromine compound in the slurry is maintained at 10 to 50 wt %;
  (iii) the solvent in the slurry contained in the vessel is a mixed solvent of a good solvent and a poor solvent for the bromine compound, the weight ratio of the good solvent to the poor solvent in the slurry is 30:70 to 60:40 and the solubility of the bromine compound in the mixed solvent is maintained at 0.1 to 5 g/100 g of the solvent; and (iv) the slurry is continuously extracted from the vessel and the solid particles of the bromine compound are separated from the slurry.

23. The continuous method for purifying a bromine compound according to claim 22, wherein the good solvent has a solubility for the bromine compound of $1/100$ g or more of the solvent and the poor solvent has a solubility for the bromine compound of 0.08/100 g or less of the solvent.

24. The continuous method for purifying a bromine compound according to claim 23, wherein the good solvent is at least one selected from the group consisting of methylene chloride, chloroform, 1,2-dichloroethane, 1,1-dichloroethane, cyclohexanone, ethyl acetate and toluene and the poor solvent is at least one selected from the group consisting of water, methanol, ethanol, i-propanol and diisopropyl ether.

25. The method for continuously purifying a bromine compound according to claim 24, wherein the purified bromine compound has bromine ion concentration of 5 ppm or less.

26. The method for continuously purifying a bromine composed according to claim 25, wherein the purified bromine compound contains 94 wt % or more of the bromine compound.

* * * * *